United States Patent
Hutchings et al.

(10) Patent No.: US 9,428,454 B2
(45) Date of Patent: Aug. 30, 2016

(54) SELECTIVE OXYGENATION OF ALKANES USING OXYGEN

(71) Applicant: University College Cardiff Consultants Limited, Wales (GB)

(72) Inventors: Graham J. Hutchings, Ross On Wye (GB); Michael M. Forde, Diego Martin (TT); Jose A. Lopez-Sanchez, Liverpool (GB); Nikolaos Dimitratos, Oxford (GB)

(73) Assignee: University College Cardiff Consultants Limited, Cardiff, Wales (GB)

( * ) Notice: Subject to any disclaimer, the term of this patent is extended or adjusted under 35 U.S.C. 154(b) by 0 days.

(21) Appl. No.: 14/351,929

(22) PCT Filed: Oct. 3, 2012

(86) PCT No.: PCT/US2012/058516
§ 371 (c)(1),
(2) Date: Apr. 15, 2014

(87) PCT Pub. No.: WO2013/058983
PCT Pub. Date: Apr. 25, 2013

(65) Prior Publication Data
US 2014/0303400 A1    Oct. 9, 2014

Related U.S. Application Data

(60) Provisional application No. 61/548,252, filed on Oct. 18, 2011.

(51) Int. Cl.
| | | |
|---|---|---|
| C07C 27/12 | (2006.01) | |
| C07C 27/16 | (2006.01) | |
| C07C 407/00 | (2006.01) | |
| C07C 29/48 | (2006.01) | |
| C07C 51/285 | (2006.01) | |

(52) U.S. Cl.
CPC ............. *C07C 407/00* (2013.01); *C07C 27/16* (2013.01); *C07C 29/48* (2013.01); *C07C 51/285* (2013.01)

(58) Field of Classification Search
CPC ..... C07C 407/00; C07C 27/16; C07C 29/50; C07C 51/285
USPC ........................................................ 562/549
See application file for complete search history.

(56) References Cited

U.S. PATENT DOCUMENTS

| 4,918,249 A | 4/1990 | Durante et al. |
| 5,132,472 A | 7/1992 | Durante et al. |
| 2007/0004944 A1 | 1/2007 | Zhan et al. |

FOREIGN PATENT DOCUMENTS

| CN | 101204664 A | 6/2008 |
| WO | 9417021 A1 | 8/1994 |

OTHER PUBLICATIONS

Raja, Applied Catalysis A: General, 1997, vol. 158, p. L7-L15.*
Fish et al, "Biomimetic Oxidation Studies." Inorganic Chemistry (1991), vol. 30, pp. 3002-3006.*
Shul'Pin, Tetrahedron Letters, 2006, 47, p. 3071-3075.*
Shul'Pin, Tetrahedron Letters, vol. 47, 2006, pp. 3071-3075.*
Busca, Chem. Rev., 2007, vol. 107, p. 5366.
Chen, Energy and Fuels, 2006, vol. 20, p. 915.
Hutchings, Nature, 2005, vol. 437, p. 1132-1135.
Khouw, Journal of Catalysis, 1994, vol. 149, No. 1, p. 195-205.
Michalkiewicz, J. Catal., 2003, vol. 215, p. 14.
Park, Appl. Catal. A, 2003, vol. 247, p. 269.
Park, Catal. Commun., 2001, 2, p. 187.
Pires, Applied Catalysis A: General, 2000, vol. 203, No. 2, p. 231-237.
Pires, Journal of Molecular Catalysis A: Chemical, 1998, vol. 136, No. 1, p. 1381-1169.
Raja, Applied Catalysis A: General, 2007, vol. 158, p. L7.
Sorokin, Chem. Commun., 2008, p. 2562.
Thomas, Nature, 1999, vol. 398, No. 6724, p. 227-230.
Yuan, Adv. Synth. Catal., 2007, vol. 349, p. 1199.
PCT/US2012/058516, Jan. 30, 2013, International Search Report and Written Opinion.
PCT/US2012/058516, Sep. 19, 2013, Written Opinion of the International Preliminary Examination Authority.
PCT/US2012/058516, Jan. 20, 2014, International Preliminary Report on Patentability.
PCT/US2012/058516, Nov. 20, 2013, Amendment Under Rule 66.
PCT/US2012/058516, Aug. 16, 2013, Response to Written Opinion.

* cited by examiner

*Primary Examiner* — Kamal Saeed
*Assistant Examiner* — Janet L Coppins
(74) *Attorney, Agent, or Firm* — Dinsmore & Shohl LLP

(57) ABSTRACT

A process for the complete or partial oxygenation of hydrocarbons comprises contacting a $C_1$-$C_8$ hydrocarbon, molecular oxygen, and hydrogen peroxide, in the presence of water and a heterogeneous catalyst, under conditions suitable to convert the $C_1$-$C_8$ hydrocarbon to at least one corresponding $C_1$-$C_8$ oxygenate product, wherein the heterogeneous catalyst provides confinement and contains both Brønsted-Lowry acid centers and Lewis acid centers. The reaction may be carried out at a temperature ranging from 2° C. to 90° C. The use of molecular oxygen increases the economic attractiveness of the process while also improving yield.

8 Claims, No Drawings

SELECTIVE OXYGENATION OF ALKANES USING OXYGEN

This application is a non-provisional application claiming priority from U.S. Provisional Patent Application No. 61/548,252, filed on Oct. 18, 2011, entitled "Selective Oxygenation of Alkanes Using Oxygen," the teachings of which are incorporated by reference herein as if reproduced in full hereinbelow.

The invention relates to processes and catalysts that convert $C_1$-$C_8$ hydrocarbons to useful partially oxygenated compounds, such as methane to methanol, under mild conditions. More particularly, it relates to use of molecular oxygen and hydrogen peroxide, in the presence of water, to convert such hydrocarbons to their corresponding partially oxygenated products.

Activation and oxygenation of lower alkanes ($C_1$-$C_8$) into useful oxygenates has long been an attractive and challenging research area. One reason for this interest is the fact that lower alkanes, especially methane ($CH_4$) and ethane ($C_2H_6$), are predominant constituents of natural gas, which is currently both abundant and inexpensive. However, activation of lower alkanes often requires severe conditions using heterogeneous catalysts, for example, a temperature greater than 500 degrees Celsius (° C.) combined with increased pressure. Under these reaction conditions the valuable oxygenate products are, unfortunately, not stable, and the formation of carbon oxides, such as carbon monoxide (CO) and carbon dioxide ($CO_2$), is usually observed.

In view of this problem, it is generally considered to be desirable to work at milder conditions, such that the formation of CO and/or $CO_2$ is reduced or eliminated and the stability of the oxygenate products formed is enhanced. To enable these milder conditions, some researchers have explored activation of $CH_4$ in the liquid phase, instead of in the gas phase. For example, B. Michalkiewicz, et al., *J. Catal.*, 215 (2003) 14, reports the oxygenation of $CH_4$ to organic oxygenates at 160° C. and a $CH_4$ pressure of 3.5 megapascals (MPa), using metallic palladium dissolved in oleum. That reference claims that methanol is obtained by the transformation of the $CH_4$ to methyl bisulfate and dimethyl sulphate, and the ester is subsequently hydrolyzed. Unfortunately, use of strong acidic media such as sulfuric acid involves corrosive, toxic reaction conditions and a large amount of waste. Other research using oleum is reported in L. Chen, et al., *Energy and Fuels*, 20 (2006) 915, wherein vanadium oxide ($V_2O_5$) in oleum is employed, at 180° C. and a $CH_4$ pressure of 4.0 MPa.

Mild conditions are also used in E. D. Park, et al., *Catal. Commun.* 2 (2001) 187, and *Appl. Catal. A*, 247 (2003) 269, wherein selective oxygenation of $CH_4$ is carried out using hydrogen peroxide generated in situ, using a palladium/carbon (Pd/C) and copper acetate ($Cu(CH_3COO)_2$) catalyst system, with trifluoroacetic acid (TFA) and trifluoroacetic anhydride (TFAA) as solvents. The Pd/C serves as an in situ generator of hydrogen peroxide ($H_2O_2$), while the $Cu(CH_3COO)_2$ serves as the oxygenation catalyst. The reaction conditions disclosed include 80° C., 5 milliliters (mL) solvent, and a total gas pressure of 47.64 standard atmospheres (atm) (4.83 MPa) (71.4 percent (%) $CH_4$, 14.3% hydrogen ($H_2$), 14.3% oxygen ($O_2$)). This process, too, requires formation of an ester followed by subsequent hydrolysis, and thus is not direct.

A method involving direct conversion of $CH_4$ to oxygenate products is disclosed in Qiang Yuan, et al., *Adv. Synth. Catal.* 349 (2007) 1199, wherein $CH_4$ is oxidized in an aqueous medium using $H_2O_2$ and homogeneous transition metal chlorides as catalysts. The transition metal chlorides may include, for example, iron chloride ($FeCl_3$), cobalt chloride ($CoCl_2$), ruthenium chloride ($RuCl_3$), rhodium chloride ($RhCl_3$), palladium chloride ($PdCl_2$), osmium chloride ($OsCl_3$), iridium chloride ($IrCl_3$), platinum hydrochloride ($H_2PtCl_6$), copper chloride ($CuCl_2$), and gold hydrochloride ($HAuCl_4$). Unfortunately, in this process recovery and reuse of the homogeneous catalyst is difficult at best.

Other researchers have also addressed the use of microstructured catalysts. For example, Raja, et al., *Appl. Catal. A: General*, 158 (1997) L7, disclose a process to oxidize $CH_4$ to methanol using phthalocyanine complexes of iron (Fe) and copper (Cu) encapsulated in zeolites as catalysts, and a combination of oxygen ($O_2$) gas and tert-butyl hydroperoxide, which is in aqueous solution, as oxidants. The process includes an autoclave reactor and a suitable solvent, such as acetonitrile, and is carried out with the tert-butyl hydroperoxide at 273 degrees Kelvin (K) (0° C.) and a reaction time of 12 hours (h). The products include methanol, formaldehyde, formic acid and $CO_2$.

Shul'pin, et al., *Tetrahedron Letters*, 47 (2006) 3071, disclose a process for the oxygenation of alkanes (including $CH_4$, $C_2H_6$, propane, n-butane, hexane, heptane, octane and nonane) using $H_2O_2$ as the oxidant to form the corresponding alcohols and ketones. The process includes an autoclave reactor with, in the case of $CH_4$, a pressure of 50 bar (5 MPa) and a reaction time of 24 h. The catalyst is a titanium-containing zeolite, "TS-1" (silicon (Si) to titanium (Ti) ratio is 20, Si/Ti=20), and while methanol is the main product, it is produced in such low amount (1.1 micromole (μmol) of methanol produced after 24 h), that potential as an industrial catalyst is not inferred.

Finally, Sorokin, et al., *Chem. Commun.*, (2008) 2562, disclose the oxygenation of $CH_4$ under mild conditions (25-60° C., 32 bar (3.2 MPa) $CH_4$ pressure, 678 μmol $H_2O_2$, and a reaction time of 20 h) using a μ-nitrido diiron phthalocyanine complex in water as a homogeneous catalyst and, additionally, a silica-supported μ-nitrido diiron phthalocyanine complex. The products include methanol, formaldehyde and formic acid, with formic acid being the major product.

Hutchings et al., *Nature*, 437 (2005) 1132-1135 discloses the oxygenation of alkenes using air and initiator (tert-butyl hydroperoxide, TBHP) with high selectivity to partial oxygenation products and significant conversions using gold supported nanoparticles under solvent free conditions. The solvent effect is shown to be important in terms of activity and selectivity, i.e., where water is used as the solvent, no formation of the desired oxygenated products is detected. The reaction is carried out at 80° C. to enable the effective decomposition of the TBHP molecule.

While researchers have identified a number of operable processes, there is still a need to identify additional processes that are both environmentally benign and economically attractive, and that desirably do not require intermediate steps or products in order to produce the desired final oxygenate products, particularly partially oxygenated products, from $C_1$-$C_8$ hydrocarbons. Specifically, the ability to use molecular oxygen as the oxidizing agent will increase the economic attractiveness of an oxygenation process over those that rely upon peroxides or other oxidizing materials for all of their oxygenation. This is even more so, when the over-oxygenation to carbon dioxide can be avoided.

In one embodiment the invention provides a process for the complete or partial oxygenation of hydrocarbons, comprising contacting a $C_1$-$C_8$ hydrocarbon, molecular oxygen, and hydrogen peroxide, in the presence of water and a heterogeneous catalyst, under conditions suitable to convert the $C_1$-$C_8$ hydrocarbon to at least one corresponding $C_1$-$C_8$ oxygenate product, wherein the heterogeneous catalyst provides confinement and contains both Brønsted-Lowry acid centers and Lewis acid centers. The reaction may be carried out at a temperature ranging from 2° C. to 200° C., preferably from 2° C. to 90° C.

The invention offers the advantages of very mild conditions with use of molecular (gaseous) oxygen, thereby improving the economics of oxygenation of lower hydrocarbons, including $C_1$-$C_8$ hydrocarbons such as, for example, methane ($CH_4$). The process involves contacting a $C_1$-$C_8$ hydrocarbon, molecular oxygen ($O_2$), and hydrogen peroxide ($H_2O_2$), in the presence of a specific heterogeneous catalyst as further described hereinbelow, and water, wherein the water and the $H_2O_2$ may be in gas phase, condensed phase, or a combination thereof. Conditions for the complete or partial oxygenation are those suitable to convert the $C_1$-$C_8$ hydrocarbon to at least one of its corresponding $C_1$-$C_8$ oxygenate or, preferably, partially oxygenated, products. By "corresponding" is meant an oxygenate product having the same number of carbon atoms as the $C_1$-$C_8$ hydrocarbon being oxygenated.

The $C_1$-$C_8$ hydrocarbon may be saturated or unsaturated, cyclic or linear, or any combination thereof. In one embodiment the hydrocarbon is $CH_4$; in another embodiment it is $C_2H_6$; in still another embodiment it is cyclohexane ($C_6H_{12}$); and in yet another embodiment it is octane ($C_8H_{18}$). Mixtures of hydrocarbons may also be selected. The hydrocarbon is desirably selected according to the target final oxygenate product(s), which may be, e.g., an alcohol, an alkyl peroxide, an aldehyde, a carboxylic acid, or a combination thereof. For example, if the desired final oxygenate product is methanol, methyl hydroperoxide, formaldehyde and/or formic acid, the selected hydrocarbon would desirably be $CH_4$.

In practicing the invention the selected hydrocarbon is brought into contact with three additional required components. The first is at least one heterogeneous catalyst. Such is, by definition, heterogeneous, meaning that it is not soluble in the $C_1$-$C_8$ hydrocarbon being converted, whether such hydrocarbon is in liquid phase, gas phase, or a combination thereof. The catalyst is further defined as containing both Brønsted-Lowry and Lewis acid centers. The nature of acid centers, and therefore identification of such centers as being of either the Brønsted-Lowry type or the Lewis-type, may be defined using any of several conventional methodologies. Among these are, for example, Temperature Programmed Desorption of Ammonia (TPD-$NH_3$); Infrared (IR) spectroscopy, based on either pyridine or $NH_3$; and Proton Magic Angle Spinning Nuclear Magnetic Resonance ($^1$H-MAS NMR), which is described in, for example, G. Busca, *Chem. Rev.*, 107 (2007) 5366.

Using such methodologies, a "Brønsted-Lowry acid center" is identified as a hydrogen ion, i.e., a proton, that is donated by the catalyst to a reaction intermediate in the inventive process's primary oxygenation reaction, i.e., the oxygenation of the $C_1$-$C_8$ hydrocarbon to form an oxygenate product. Determination of whether a given solid catalyst candidate donates a proton in a reaction may be carried out by, for example, IR spectroscopy, wherein a pyridine is made available for adsorption by the catalyst candidate. The presence of a Brønsted-Lowry acid center is confirmed if vibrations corresponding substantially to 1640, 1628, 1544, and 1492 $cm^{-1}$ are recorded. These measurements represent a protonated pyridine complex, which means that a pyridinium ion has been formed, indicating the presence of a Brønsted-Lowry acid center in the catalyst.

A "Lewis acid center" is identified as a coordinatively-unsaturated metal cation. As used herein, the phrase "coordinatively-unsaturated metal cation" means that the catalyst contains a metal cation that is capable of forming a coordination complex with an available ligand. In the primary oxygenation reaction of the inventive process, the coordinatively unsaturated metal cation, for example, an aluminum ($Al^+$) or iron ($Fe^+$) cation having a low-lying vacant orbital, can serve as an electron acceptor. Determination of whether a given solid catalyst candidate accepts one or more electrons in a reaction may be carried out by, for example again, IR spectroscopy, wherein a pyridine is made available for adsorption by the catalyst candidate. The presence of a Lewis acid center is confirmed if vibrations corresponding substantially to 1624, 1618, and 1597 $cm^{-1}$ are recorded. These vibrations are attributed to three different coordinatively complexed pyridine species, which means that a coordinative metal cation is present in the catalyst. Such coordinative metal cation is, by definition, a Lewis acid center.

It is notable that, in the catalysts that are useful in the inventive process, both Lewis and Brønsted-Lowry acid centers are present. Such may be both located on the surface of the catalyst, or, in the case of, for example, some types of porous crystalline catalysts, the Lewis acid centers may be located primarily on the exterior surface, while the Brønsted-Lowry acid centers may be located primarily in the interior of the pores. Alternatively, Lewis acid centers may be added to a catalyst that, in its as-synthesized form, contains only Brønsted-Lowry acid centers in pores thereof, by simply adding thereto a modifying metal heterocation, such as $Fe^+$. This step will incorporate Lewis acid centers into the pores. Another effective approach, particularly useful where the starting catalyst is an aluminosilicate microporous material, is to treat the catalyst with steam at a temperature sufficient to cause dealumination of the structure within the micropores. The result of this dealumination is formation of Lewis acid centers in the micropores. It is generally within the understanding of those skilled in the art that suitable catalysts may display different amounts and strengths of Brønsted-Lowry-type and/or Lewis-type acidity on the same surface, depending upon the composition and structure of the catalyst, as well as the method of any given catalyst's preparation and any post-synthesis treatment(s) it may receive. The strength and the ratio of Lewis acid centers to Brønsted-Lowry acid centers will often affect the conversion and distribution of the obtained oxygenate products. For example, increasing the strength of both Lewis acid and Brønsted-Lowry acid sites leads to a progressive increase in alkane conversion, i.e., yield, of oxygenate products in general, while the selectivity to specific products may be varied by altering the ratio of Lewis acid centers to Brønsted-Lowry acid centers.

As noted hereinabove, the selected catalyst is capable of providing confinement of the $C_1$-$C_8$ hydrocarbon molecules being oxidized. The term "confinement" as used herein means that the catalyst has a structure including pores, and that the pore dimensions are capable of at least partially admitting and holding (i.e., "confining") the selected $C_1$-$C_8$ hydrocarbon molecules, thereby altering the admitted molecules' structure and reactivity in some way. Another way of stating this is that the critical diameter of the selected $C_1$-$C_8$ hydrocarbon molecule is smaller than the average cross-sectional diameter of the pores. These pores may be micropores, having a diameter less than 2 nanometers (nm);

mesopores, having a diameter from 2 nm to 50 nm; and/or macropores, having a diameter greater than 50 nm; with the characterization of a catalyst as being microporous, mesoporous, or macroporous being based on its predominant average pore diameter. In certain particular embodiments the catalyst is a molecular sieve, i.e., a microporous solid material, and preferably a molecular sieve including silicon (Si) and oxygen (O), for example, in the form of an oxide of silicon, i.e., silicon dioxide ("silica," $SiO_2$). Such molecular sieve may also include, in its structure and not as a modifying metal or modifying metal oxide, aluminum (Al), for example, in the form of an oxide of aluminum, e.g., aluminum oxide ("alumina," $Al_2O_3$). Where both silica and alumina are present, the result is an aluminosilicate molecular sieve, which is also called a zeolite. Such may be naturally-occurring or synthetic, having a structure defined by the International Zeolite Association. Of particular effect may be those having a structure defined as an "MFI" type, such as those designated with the "ZSM" prefix, and of these the zeolite designated as "ZSM-5" may in some embodiments be preferred. The selected material may have a wide range of ratios of $SiO_2/Al_2O_3$, ranging from 20 to 10,000. Other materials characterized as zeolites or zeotypes (i.e., artificial structures synthesized to correspond to defined zeolite structures), including but not limited to those having a beta structure, a mordenite structure, a ferrierite structure, a faujasite structure, a rho structure, or a chabazite structure, and combinations of such materials, may also be useful in the inventive process, provided such contain both Brønsted-Lowry and Lewis acid centers as described hereinabove. Further non-limiting examples include a variety of other zeolites, such as Zeolite-Y, Zeolite Beta (Zeolite-β), and Ferrierite.

The catalyst structure may be crystalline, amorphous, or a combination thereof, and in certain particular embodiments may include a relatively small amount of a modifying metal and/or a modifying metal oxide. Such modifying metal and/or modifying metal oxide is, by definition, different from any metals included in the primary structure of the catalyst, and may be selected from aluminum (Al), gallium (Ga), iron (Fe), zinc (Zn), copper (Cu), titanium (Ti), and phosphorus (P); oxides thereof; and combinations thereof; in an amount ranging from 10 parts per million (ppm), i.e., a trace amount, to 10% by weight (wt %), based on the total weight of the catalyst. In preferred embodiments the amount may range from 1 wt % to 5 wt %, on the same basis. Thus, in one embodiment the catalyst may have a microporous crystalline aluminosilicate structure, further including a modifying metal or metal oxide other than Al or $Al_2O_3$, while in another embodiment the catalyst may have a silicate structure, and include a modifying metal or metal oxide such as, in non-limiting examples, Al, $Al_2O_3$, Ga, Fe, CuO $Cu_2O$, or combinations thereof. Preferred catalysts may include iron modified versions of the ZSM-5 zeolite, e.g., those including from 10 ppm to 10 wt % of iron, based on the weight of the ZSM-5 zeolite, which is a metal-promoted aluminosilicate catalyst. Also preferred are metal-promoted silicalite catalysts, the silicalites being the silica analogues of ZSM-11.

The catalyst may be either supported or unsupported, or may serve simultaneously as both catalyst and support, and may be formed by a variety of methods. For example, in unsupported form the catalyst may be used as a crystalline or amorphous powder. Where a supported catalyst is desired, the catalyst may be combined with a binder into an extrudate or pellets for added strength and durability; may be deposited on or in a support material; or may be formed as a membrane. Support materials may be selected from, for example, ceramic materials, defined as inorganic non-metallic solids prepared by heating followed by cooling, including but not limited to oxides, such as zirconia; non-oxides such as carbides, nitrides, borides and silicides; other solids such as metals and alloys, for example, materials based on carbon, nickel, cobalt, molybdenum, and stainless steels; and combinations thereof. In certain embodiments, where a gas stream such as $CH_4$ or $C_2H_6$ is to be oxidized, it may be particularly convenient to use a solid, supported catalyst.

The catalyst may be synthesized and/or modified, via post-synthesis treatment, by a method selected from, for example, hydrothermal synthesis, impregnation, deposition-precipitation, sol immobilization, sublimation, chemical vapor infiltration, or a combination thereof. In one embodiment it may be desirable to calcine the catalyst after it has been prepared, in order to increase its activity; in another embodiment it may be useful to reduce the catalyst with hydrogen; and in a third embodiment it may be useful to treat the catalyst in water vapor, e.g., steam, which may increase its selectivity to a desired target alcohol product. When the catalyst has been prepared by chemical vapor infiltration, washing the catalyst with acetone or an acid following preparation may desirably improve its activity and/or selectivity. Those skilled in the art will be able to determine, with routine experimentation at most, which, if any, of these synthesis and modification treatments may be most useful to obtain a catalyst best geared toward a given target product or product mix.

Synthetic zeolites useful in the inventive process may be prepared by slow crystallization of, in one embodiment, a silica-alumina gel in the presence of an alkali and an organic template. The product properties depend upon reaction mixture composition, pH of the system, operating temperature, pre-reaction and reaction times, and template used. One such process is a sol-gel method. In that method, other elements, including, for example, modifying metals and/or modifying metal oxides, may be conveniently incorporated in the zeolite structure. A calcination pre-treatment (i.e., post-synthesis, but prior to use in the inventive process), at a temperature from 200° C. to 800° C., preferably from 400° C. to 700° C., to increase the activity and/or alter the selectivity of the final catalyst prior to using it, may be particularly useful for zeolites. Such pre-treatment may be performed in a static or flow procedure in a diluent selected from air, $H_2$, an inert gas, and combinations thereof. Water vapor may optionally be included with the diluent.

The inventive process includes contacting the selected $C_1$-$C_8$ hydrocarbon, the molecular $O_2$, and the $H_2O_2$ in the presence of water. In order to do this, in one non-limiting embodiment the hydrocarbon may be fed, with or without a diluent, in gas phase or condensed phase (condensed phase being, accordingly, a solid, a combination of a solid and a liquid, e.g., a dispersion or slurry, or a combination of a gas and a liquid, e.g., an aerosol), to a reaction vessel containing the heterogeneous catalyst. There the heterogeneous catalyst, for example, an iron-modified ZSM-5 zeolite, activates the $C_1$-$C_8$ hydrocarbon, molecular $O_2$, water, and $H_2O_2$ mixture to form one or more corresponding at least partially oxidized products ("oxygenate products"). Such products may include, for example, an alcohol that corresponds to, i.e., has the same number of carbon atoms as, the starting $C_1$-$C_8$ hydrocarbon. In certain embodiments the reaction may be carried out at a temperature ranging from 2° C. to 200° C., preferably from 2° C. to 90° C., more preferably from 20° C. to 80° C., and most preferably from 30° C. to 70° C. For example, some of the described heterogeneous zeolite catalysts may effectively catalyze the reaction of $CH_4$, gaseous oxygen, and $H_2O_2$ in water to form methanol ($CH_3OH$), using a temperature as low as 2° C., with minimal losses to CO or $CO_2$ as by-products. In certain embodiments the amount of water may range from trace (10 ppm) levels to 50 wt % or higher, based on the combined weight of water, $C_1$-$C_8$ hydrocarbon, and $H_2O_2$, and a minimum of 50 wt % of water may be preferred, particularly in condensed phase reactions. Also in particular embodiments, the process may be effectively conducted to maintain a total system pressure ranging from 1 to 140 atm (0.101 MPa to 14.19 MPa), more preferably from 8 to 100 atm (0.81 MPa to 10.13 MPa), and most preferably from 20 to 70 atm (2.03 MPa to 7.09 MPa). Moreover, it may be desirable that the process be conducted such that, where the $C_1$-$C_8$ hydrocarbon is not entirely in solution, any amount thereof that is in gas phase be maintained within a similar pressure range. In one particular embodiment, the process may be carried out entirely in gas phase, as either a continuous or cyclic process.

The amounts of molecular oxygen and hydrogen peroxide that are used to react with the selected $C_1$-$C_8$ hydrocarbon are preferably effective to at least partially oxidize the hydrocarbon to its corresponding target oxygenate product(s). Because molecular $O_2$ is generally much less expensive than neat $H_2O_2$, it is generally desirable to maximize the amount of $O_2$ and minimize the amount of $H_2O_2$ such that the majority, if possible, of the incorporated oxygen in the $C_1$-$C_8$ oxygenate comes from the molecular oxygen and not from the hydrogen peroxide. The source of the oxygen being incorporated may be determined using $^{18}O_2$ in a gas chromatography-mass spectroscopy (GC-MS) analysis. At the same time it is desirable to avoid over-oxygenation of the $C_1$-$C_8$ hydrocarbon to form undesired products, e.g., where over-oxygenation will result in alkyl peroxides, aldehydes, and/or carboxylic acids, in cases where alcohols are desired. Those skilled in the art will be aware that it is also advisable to ensure that the molar ratio of molecular $O_2$ to $H_2O_2$, and the $C_1$-$C_8$ hydrocarbon and diluent pressures, are selected to avoid potentially explosive combinations. In general it is desirable that the molar ratio of molecular $O_2$ to $H_2O_2$ range from 1:10, preferably from 1:5, more preferably from 1:1, and most preferably from 10:1.

Following formation of the desired target oxygenate product or mixture of products, appropriate separation steps may be carried out where necessary. Standard separation means and methods may be employed. Where the catalyst or combination of catalysts is/are solid and insoluble in either liquid or gas phase, such may be conveniently separated using simple filtration, and optionally then appropriately regenerated and/or recycled back into the same or a different reaction process. Regeneration steps may include, for example, burning off any build-up on the catalyst or treating the catalyst with a fresh hydrogen peroxide solution. The catalyst may also be subjected to such regeneration periodically, according to need. Thus, the process of the invention may be operated as a batch, semi-batch, or continuous process.

EXAMPLES

In the Examples the following are used without further purification from BOC Gases: $CH_4$, 99.999% purity, $^{18}O_2$ 99% of $^{18}O$ atom purity, $^{16}O_2$ 99.99% purity. The gas mixture of the reactor is removed using a gas sampling bag and analysis is performed using GC. Liquid-phase products are analyzed using high performance liquid chromatography (HPLC) or proton nuclear magnetic resonance ($^1$H-NMR). Deuterium oxide ($D_2O$) is used as the lock reference. In the $^1$H-NMR analysis, a sealed capillary tube is prepared with a solution of tetramethylsilane (TMS) and chloroform ($CHCl_3$). $H_2O_2$ yield is determined by titration of aliquots of the final filtered solution with acidified cesium sulphate ($Ce(SO_4)_2$) solutions, which have been standardized against hydrated ammonium ferrosulphate $(NH_4)_2Fe(SO_4)_2 \cdot 6H_2O$ using ferroin as the indicator. The commercially available catalyst, Zeolite ZSM-5, is obtained from Zeolyst International, and samples of the Zeolite ZSM-5 are calcined in static air at 600° C. prior to use in the Examples unless indicated otherwise. A parenthetical number immediately following the zeolite name, e.g., "(30)," indicates the molar ratio of $SiO_2/Al_2O_3$ as provided by the supplier. Iron acetylacetonate ($Fe(C_5H_7O_2)_3$) having a purity greater than 99.95% is supplied by Sigma Aldrich.

Preparation of a Fe/ZSM-5 (30) Catalyst by Chemical Vapor Infiltration (CVI).

Fe/ZSM-5 (30) catalyst is prepared by CVI as follows. A 1 gram (g) sample of commercially obtained ZSM-5 (30) zeolite is treated under vacuum for 2 h. A commercial sample of iron acetylacetonate ($Fe(C_5H_7O_2)_3$ (0.0774 g), corresponding to a nominal final metal loading of 1.1 wt %, is then mixed with the vacuum-treated ZSM-5 zeolite. The mixture is placed under vacuum and heated to 150° C. for 2 h. The material is then removed and calcined in air at 400° C. for 3 h.

Comparative Example A

Liquid Phase Oxygenation of $CH_4$ with $H_2O_2$ Using a Fe/ZSM-5 (30) CVI Catalyst Catalytic oxygenation of $CH_4$ is carried out using a stainless-steel autoclave (Parr reactor) containing a Teflon™-lined vessel with a total volume of 50 mL. A measured amount of Fe/ZSM-5 zeolite synthesized by CVI (0.028 g) is charged to the vessel, which has already been charged with a 10 mL solution of distilled water and an amount of $H_2O_2$ (50 wt %, 0.005 mole (mol)). The total volume of the reaction solution is 10 mL. Air in the reactor is removed by purging 3 times with $CH_4$ at 200 pounds per square inch (psi) (13.61 bar, 1.37 MPa), and then the system is pressurized with $CH_4$ and/or $O_2$ to a fixed pressure (440 psi, 3.03 MPa, 0.03 mol). The autoclave is heated to 50° C. Once respective reaction temperature is attained, the solution is vigorously stirred at 1500 revolutions per minute (rpm) and maintained at the reaction temperature for 0.5 h to enable completion of each respective oxygenation reaction. At the end of the reaction the autoclave is cooled with ice to a temperature of 12° C. to minimize the $CH_3OH$ volatility and loss. Products of the reaction are subsequently analyzed and results are shown in Table 1.

Comparative Example B

Liquid Phase Oxygenation of $CH_4$ with $H_2O_2$ Using a Fe/ZSM-5 (30) CVI Catalyst According to the method of Comparative Example A, a liquid phase oxygenation of $CH_4$ is carried out using a Fe/ZSM-5 (30) CVI catalyst, with the exception that the catalyst loading is 0.054 g, reaction volume is 20 mL, the $H_2O_2$ concentration is 1 M, and the total reactor pressure is 5.5 bar (0.55 MPa). Products of the reaction are subsequently analyzed and results are shown in Table 1.

Comparative Example C

Liquid Phase Oxygenation of $CH_4$ with Molecular $O_2$ Using a Fe/ZSM-5 (30) CVI Catalyst According to the method of Comparative Example A, a liquid phase oxygenation of $CH_4$ is carried out using a Fe/ZSM-5 (30) CVI catalyst, with the exception that no $H_2O_2$ is added to the reaction mixture and a gas phase composition 85.7:14.3 mole/mole ratios of $CH_4$ and $^{16}O_2$ is used in total pressure of 35 bar (3.5 MPa). This corresponds to the same amount of 'O' from $H_2O_2$ as in Comparative Example A. Products of the reaction are subsequently analyzed and results are shown in Table 1. No products are detected when molecular $O_2$ is used as the sole oxidant.

Example 1

Liquid Phase Oxygenation of $CH_4$ with $H_2O_2$ and Molecular $O_2$ Using a Fe/ZSM-5 (30) CVI Catalyst The liquid phase oxygenation of $CH_4$ with $H_2O_2$ in the presence of molecular $O_2$ is carried out according to the method of Comparative Example A, while using a 96.5:3.5 mole/mole ratio of $CH_4$ and $^{18}O_2$. Products of the reaction are subsequently analyzed and results are shown in Table 1.

The reaction filtrate from Example 1 is analyzed by LC-MS as follows: The as-filtered aqueous reaction mixture is infused into an electro-spray source operating at capillary voltage of 3.5 kilovolts (kV) and cone voltage of 100 volts (V). The spectrometer is operated in EI-mode (electro-spray ionization negative mode), such that the major reaction product, formic acid (HCOOH) as determined separately by $^1$H-NMR, can be observed in its de-protonated dimeric/trimeric form. Dimers of HCOOH are observed with incorporation of one $^{18}O$ per dimer, i.e., one labeled oxygen atom out of 4 oxygen atoms per dimer. In total 6% incorporation of $^{18}O_2$ is observed by integration of the peaks obtained from this analysis. The product analysis shows an increase in oxygenate productivity when $^{18}O_2$ is present in the reaction.

Example 2

Liquid Phase Oxygenation of $CH_4$ with $H_2O_2$ and Molecular $O_2$ using a Fe/ZSM-5 (30) CVI Catalyst The liquid phase oxygenation of $CH_4$ with $H_2O_2$ in the presence of molecular $O_2$ is carried out according to the method of Comparative Example B, while using a 96.5:3.5 mole/mole ratio of $CH_4$ and $^{16}O_2$. Products of the reaction are subsequently analyzed and results are shown in Table 1. A 53% increase in oxygenate productivity is observed under these conditions in the presence of $^{16}O_2$.

TABLE 1

Activity and effect of reaction conditions on methane oxygenation with Fe/ZSM-5 (30) CVI calcined.

| | Reaction conditions | | Product amount (μmol) | | | | Oxygenate | Oxygenate |
|---|---|---|---|---|---|---|---|---|
| Example | P, bar | [$H_2O_2$] (M) | $^1$MeOH [a] | $^2$HCOOH [a] | $^3$MeOOH [a] | $CO_2$ [b] | productivity [c] | selectivity (%) |
| Comp A | $^4$30.5 | 0.5 | 16 | 54 | 16 | 9 | 6.2 | 91 |
| Comp. B | $^4$5.5 | 1 | 11 | 121 | 10 | 24 | 5.3 | 85 |
| Comp. C | $^4$35.0 | 0 | 0 | 0 | 0 | 0 | 0 | n/a |
| Example 1 | $^4$30.5 | 0.5 | 15 | 75 | 3 | 25 | 6.7 | 79 |
| Example 2 | $^4$5.5 | 1 | 5 | 214 | 1 | 35 | 8.1 | 86 |

$^1$Methanol
$^2$Methanoic (formic) acid
$^3$Methyl hydroperoxide
$^4$30.5 bar = 3.05 MPa, 5.5 bar = 0.55 MPa, 35.0 bar = 3.5 MPa
[a] = analyzed by $^1$H-NMR with 1% TMS in deuterated chloroform ($CDCl_3$) as the internal standard
[b] = analyzed by gas chromatograph with flame ionization detector (GC-FID); values obtained based on $CO_2$ calibration curve
[c] = calculated as "moles (oxy) $kg^{-1}$ (cat) $h^{-1}$"

What is claimed is:

1. A process for the complete or partial oxygenation of hydrocarbons, comprising contacting a $C_1$-$C_3$ alkane, molecular oxygen, and hydrogen peroxide, in the presence of water and a heterogeneous catalyst, under conditions suitable to convert the $C_1$-$C_3$ alkane to at least one corresponding $C_1$-$C_3$ oxygenate product, wherein the heterogeneous catalyst provides confinement of the $C_1$-$C_3$ alkane molecule, contains both Brønsted-Lowry acid centers and Lewis acid centers, and is selected from iron modified heterogeneous catalysts; and the conditions include a total system pressure of at least 0.81 megapascals.

2. The process of claim 1, wherein the conditions include a temperature from 2° C. to 90° C.

3. The process of claim 1, wherein the conditions include a total system pressure of from 0.81 megapascals to 14.19 megapascals.

4. The process of claim 1, wherein the $C_1$-$C_3$ alkane is methane and the methane oxygenate product is selected from methanol, formic acid, methyl hydroperoxide, formaldehyde, and combinations thereof.

5. The process of claim 1, wherein the conditions include the $C_1$-$C_3$ alkane and the hydrogen peroxide being in a phase selected from (a) a condensed phase; (b) a gas phase; and (c) a combination thereof.

6. The process of claim 1, wherein the catalyst includes silicon, oxygen, and optionally a second modifying metal or modifying metal oxide selected from the group consisting of aluminum, gallium, zinc, copper, titanium, phosphorus, oxides thereof, and combinations thereof.

7. The process of claim 6, wherein the catalyst includes an oxide of silicon, an oxide of aluminum, or a combination thereof, and is crystalline, amorphous, or a combination thereof.

8. The process of claim 1, wherein the molar ratio of molecular oxygen to hydrogen peroxide ranges from 1:10 to 10:1.

* * * * *